United States Patent
Mousa et al.

(10) Patent No.: US 9,700,042 B2
(45) Date of Patent: Jul. 11, 2017

(54) NANOFORMULATION OF MUSK-DERIVED BIOACTIVE INGREDIENTS FOR NANOCOSMETIC APPLICATIONS

(71) Applicants: Shaker A. Mousa, Wynantskill, NY (US); Amna Saddiq, Jeddah (SA)

(72) Inventors: Shaker A. Mousa, Wynantskill, NY (US); Amna Saddiq, Jeddah (SA)

(*) Notice: Subject to any disclaimer, the term of this patent is extended or adjusted under 35 U.S.C. 154(b) by 51 days.

(21) Appl. No.: 14/614,849

(22) Filed: Feb. 5, 2015

(65) Prior Publication Data
US 2015/0223451 A1 Aug. 13, 2015

Related U.S. Application Data

(60) Provisional application No. 61/936,919, filed on Feb. 7, 2014.

(51) Int. Cl.
*A01N 25/10* (2006.01)
*A01N 25/28* (2006.01)

(52) U.S. Cl.
CPC ..................................... *A01N 25/28* (2013.01)

(58) Field of Classification Search
None
See application file for complete search history.

(56) References Cited

U.S. PATENT DOCUMENTS

| | | | |
|---|---|---|---|
| 7,338,928 B2* | 3/2008 | Lau | A61K 8/11 424/401 |
| 2013/0149385 A1* | 6/2013 | Mousa | A61K 9/5161 424/493 |

OTHER PUBLICATIONS

Bauer, A.W., et al., Antibiotic susceptibility testing by a standard single disk diffusion method, Amer. J. Clin. Pathol. 45:493-496 (1966).

Bell, S.C. and W.E. Grundy, Preparation of Agar Wells for Antibiotic Assay. Applied Microbiology, Applied Microbiology, vol. 16, No. 10, pp. 1611-1612 (Oct. 1968).

* cited by examiner

*Primary Examiner* — Layla Berry
(74) *Attorney, Agent, or Firm* — Schmeiser, Olsen & Watts, LLP

(57) ABSTRACT

The composition of the Nano carrier or Nano polymers composed of Hyaluronic Acid (15-25%) and fatty acids (50-70%) cross linked with ultra-Low molecular weight chitosan (15-25%) encapsulating isolated compounds from musk and their combinations for cosmetic use as anti-aging, anti-microbial, and fragrance. Additionally, these nano-encapsulated Musk bioactive compounds (MBC) at 0.1-10% (w/w MBC/Nano polymers) could be used in textile manufacturing (carpet/rugs and clothes) to provide anti-microbial and fragrance properties. Furthermore, Musk derived products are chemically conjugated to HA polymer, FA polymer, CH polymer, HA-CH co-polymer, FA-CH co-polymer or HA-CH-FA co-polymer to be incorporated into the fabric of the textile products (carpet/rugs or clothes).

8 Claims, 5 Drawing Sheets

US 9,700,042 B2

NANOFORMULATION OF MUSK-DERIVED BIOACTIVE INGREDIENTS FOR NANOCOSMETIC APPLICATIONS

RELATED APPLICATION

The present invention claims priority to U.S. Provisional No. 61/936,919, filed on Feb. 7, 2014, which is incorporated herein by reference in its entirety.

FIELD OF THE INVENTION

The present invention relates to a nanoformulation applicable to cosmetic and textile (carpet/rugs, and clothes) manufacturing for providing fragrance and antimicrobial properties in cosmetic and textile products.

BACKGROUND OF THE INVENTION

Existing textile (carpet/rugs, and clothes) products might easily be a carrier of different microbes from the environment including bacteria, fungi and certain viruses along with bed smells. Additionally, having naturally driven anti-microbial with fragrance in cosmetic could be extremely valuable for infection prevention while it has appealing smell.

Hence, there is a need for naturally driven anti-microbial with appealing musk fragrance to be impeded within the cosmetic products and to be impeded within the polymeric fibers of the different textile products.

SUMMARY OF THE INVENTION

The present invention provides a composition, comprising: a nano-polymer comprising hyaluronic acid (HA polymer) and fatty acids (FA Polymer) cross linked with chitosan (CH) resulting in HA-CH, FA-CH or HA-CH-FA; and compounds encapsulated within the nano-polymer, said compounds derived from musk. Additionally, musk derived products are chemically conjugated to HA polymer, FA polymer, CH polymer, HA-CH co-polymer, FA-CH co-polymer or HA-CH-FA co-polymer to be incorporated into the fabric of the textile products (carpet/rugs or clothes).

BRIEF DESCRIPTION OF THE DRAWINGS

In FIG. 1-5, Musk derived products such as M1 and/or M2 are chemically conjugated to HA polymer, FA polymer, CH polymer, HA-CH co-polymer, FA-CH co-polymer or HA-CH-FA co-polymer to be incorporated into the fabric of the textile products (carpet/rugs or clothes).

DETAILED DESCRIPTION OF THE INVENTION

Figure 1:
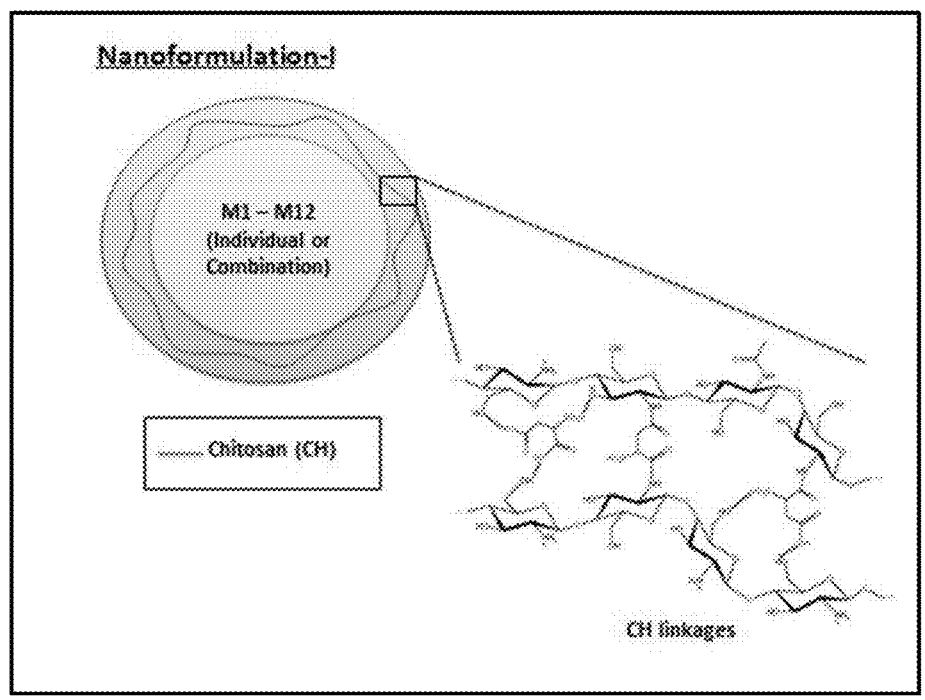
FIG. 1 depicts Nano-encapsulation of musk derived bioactive compounds (M1 and/or M2) with anti-microbial and fragrance characteristics using natural chitosan (derived from mushroom) cross-linked nano-polymer, in accordance with embodiments of the present invention.

The present invention provides a nanoformulation applicable that may be used for cosmetic and textile manufacturing to providing fragrance and antimicrobial properties in cosmetic and textile products such as carpet, rugs or clothes.

Hyaluronic acid (HA) is present in the extracellular matrix in the basal layer of the epidermis and it promotes keratin productions which affect skin hydration. HA also interacts with a cell-surface glycoprotein to support collagen synthesis and normal skin function.

Fatty acids (FA) derived from different types of musk including white musk and others. FA examples—Tetradecanoic acid, other fatty acids isolated from Musk as shown in the detailed isolated FA.

Chitosan (CH) is derived from mushroom and processed to produce low to ultra-low molecular weight for cross bridging with HA and FA.

Musk derived products such as M1 and/or M2 are chemically conjugated to HA polymer, FA polymer, CH polymer, HA-CH co-polymer, FA-CH co-polymer or HA-CH-FA co-polymer to be incorporated into the fabric of the textile products (carpet/rugs or clothes).

Encapsulation of different ingredients isolated from musk and derivatives include: P-Anisaldehyde, P-hydroxyacetophenone, 3-hydroxy P-Anisaldehyde, and their combination for synergistic anti-microbial activity encapsulated into HA-FA-CH Nanoparticles having 100-300 nm and zeta potential of +5 to 20 mv. Using Honey for wound dressing.

List all isolated aromatic compounds that are isolated and synthesized having anti-microbial activity to be encapsulated in the above Nano carrier (Tables and FIGS. below).

Antimicrobial efficacy of 3-hydroxyl p-Anisaldehyde ($C_8H_8O_3$) and p-Hydroxy-acetophenone (C8H8O2) compounds:

EXAMPLE 1

Materials and Methods
(i) Musk: Natural Musk (animal Musk) used in this study was extracted from navel (deer) as a powder.
(ii) Test organisms:
  Pathogenic Fungi: *Aspergillus niger, Aspergillus fumigatus, Aspergillus flavus, Fusarium oxysporum* and *Candida albicans* were cultured on sabaroud dextrous agar media (Oxioid CM 41) at 25° C.
  Pathogenic bacteria: *Staphylococcus aureus* and *Pseudomonas aeroginosa* were cultured on Mueller Hinton media (Oxioid CM 41) at 37° C.

EXAMPLE 2

Extraction of non-alkaloid compounds from musk: 6 g of lipid free musk powder were placed into a soxhlet apparatus and extracted with 50 ml methanol for 8 hours at a temperature of 40-60° C. The filtered solution was then concentrated to dryness under vacuum at 45° C. The obtained dry extract was mixed with acidic water (PH=2). The supernatant was filtered through a 0.22-μm nylon membrane. The filtrate was then extracted by diethyl ether using separating funnel. The layer of diethyl ether was then separated and evaporated. The obtained gummy residue was then subjected to thin layer chromatography using petroleum ether and ethyl acetate for separating the active compounds. Two compounds were separated namely hydroxyl p-Anisaldehyde (C8H8O3) (0.011 g) (Rf=0.47) and p-Hydroxyacetophenone $C_8H_8O_2$)(0.009 g) (Rf=0.47). The two compounds were identified by GC mass and HPLC.

EXAMPLE 3

Figure 2:
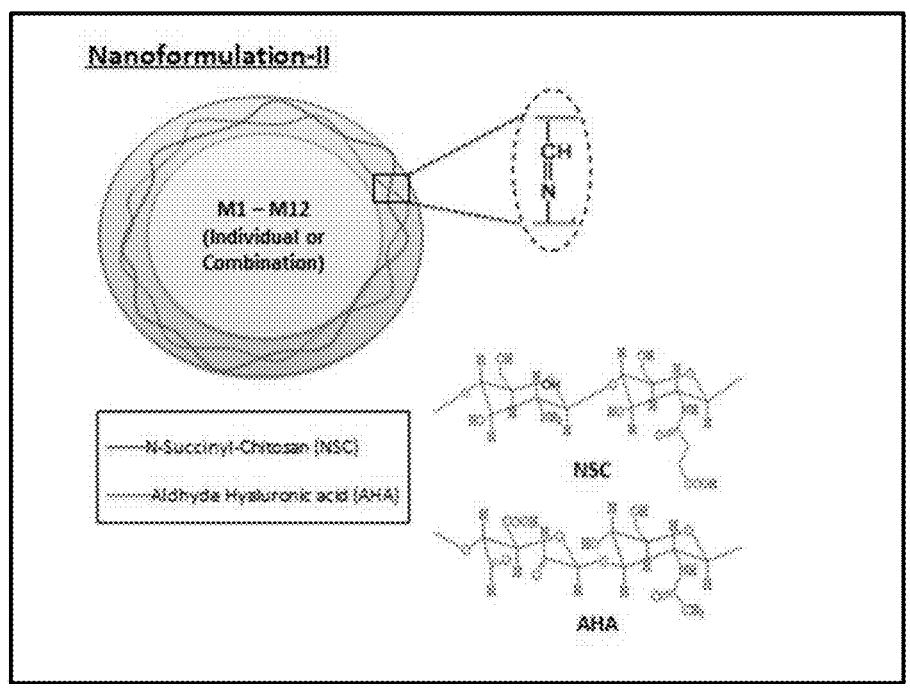
FIG. 2 depicts Nano-encapsulation of musk derived bioactive compounds (M1 and/or M2) with anti-microbial and fragrance characteristics using natural chitosan cross linked with Hyaluronic acid, in accordance with embodiments of the present invention.

HPLC Analysis of separated compounds: The hydroxyl p-Anisaldehyde ($C_8H_8O_3$) and p-Hydroxyacetophenone were quantified by HPLC coupled with UV detection (HPLC-UV). HPLC analysis was performed with an HPLC instrument (Agilent 1100, USA) equipped with a quaternary solvent delivery system, a column oven, and an UV detector (Agilent 1100, VWD, USA). Twenty microliters of sample solution were injected into the column manually. Separation was achieved on an Hypersil ODS2 column (4.6 mm×250 mm, 5 μm) from Dalian Elite Analytical Instruments Co., Ltd. The column temperature was set to 25° C. and the detection wavelength was set at 280 nm. The mobile phase was 25% methanol with isocratic elution at a flow rate of 1.0 ml/min. FIGS. 1 and 2 show a chromatogram for the simultaneous determination of the two compounds respectively

EXAMPLE 4

Biological activity: Antimicrobial activities of the 3-hydroxyl p-Anisaldehyde ($C_8H_8O_3$) and p-Hydroxy-acetophenone (C8H8O2) compounds were tested against the fungal species *Aspergillus niger, Aspergillus fumigatus, Aspergillus flavus, Fusarium oxysporum* and *Candida albicans*. Also both tested compounds were tested the bacterial species *Staphylococcus aureus* and *Pseudomonas aeroginosa*.

EXAMPLE 5

Antifungal activities: The agar disc diffusion method was used to evaluate the antifungal activities of the tested compounds (Bauer, A.W., et al., Antibiotic susceptibility testing by a standard single disk diffusion method, Amer. J. Clin. Pathol. 45:493-496 (1966)). 50 ml of sabaroud dextrous agar media contained 1 ml from Suspension of fungi, then poured into sterile Petri dishes (9 cm in diameter) and left to solidify. Filter paper discs (6 mm in diameter) were soaked with 20 μl of the stock solutions (0.5 ml of the 3-hydroxyl p-Anisaldehyde($C_8H_8O_3$) and p-Hydroxyacetophenone ($C_8H_8O_2$) dissolved in Chloroform ($CHCl_3$)(100.0 μgml$^{-1}$)) and placed on the inoculated plates. The diameter of the inhibition zones were measured in millimeters after 4 days at 25±2° C. Table (1).

EXAMPLE 6

Antibacterial activities: Antibacterial activities of the tested compounds were employed by used the agar disc diffusion method Hasenekoğlu (1990). Suspension of the tested bacteria ($10^6$ CFU/μl ,O.D was measured calorimetry using spectrophotometer (Spectro, labomed, Inc.) at 620 mm) were spread on Mueller Hinton Agar (Oxioid). Each test solutions was prepared in $CHCl_3$ filter paper discs (6 mm in diameter) were soaked with 20 μl of the stock solutions and placed on the inoculated plates. The diameter of the inhibition zones were measured in millimeters after 24 h at 37° C. The results were confirmed using another method which was the agar well diffusion method would be employed for the determination of antibacterial and antifungal activities of 3-hydroxyl p-Anisaldehyde ($C_8H_8O_3$) and p-Hydroxyacetophenone ($C_8H_8O_3$) at and 0.5% (Bell, S.C. and W.E. Grundy, Preparation of Agar Wells for Antibiotic Assay. Applied Microbiology, Applied Microbiology, Vol. 16, No. 10, pp. 1611-1612 (Oct. 1968)).

EXAMPLE 7

Anti-Microbial Activities: The results showed that the 3-hydroxyl p-Anisaldehyde ($C_8H_8O_3$) and p-Hydroxyacetophenone ($C_8H_8O_3$) have the ability to inhibit the growth of tested microorganisms fungi and bacteria. Inhibition clear zones were observed around the filter paper discs (Table 1). From the results it was observed that the best inhibition of Pathogenic bacteria and fungi were obtained when using the two compounds together who use each one separately.

FIG. 1 depicts Nano-encapsulation of musk derived bioactive compounds (M1 and/or M2) with anti-microbial and fragrance characteristics using natural chitosan (derived from mushroom) cross linked nano-polymer, in accordance with embodiments of the present invention.

FIG. 2 depicts Nano-encapsulation of musk derived bioactive compounds (M1 and/or M2) with anti-microbial and fragrance characteristics using natural chitosan cross linked with Hyaluronic acid, in accordance with embodiments of the present invention.

Figure 3:
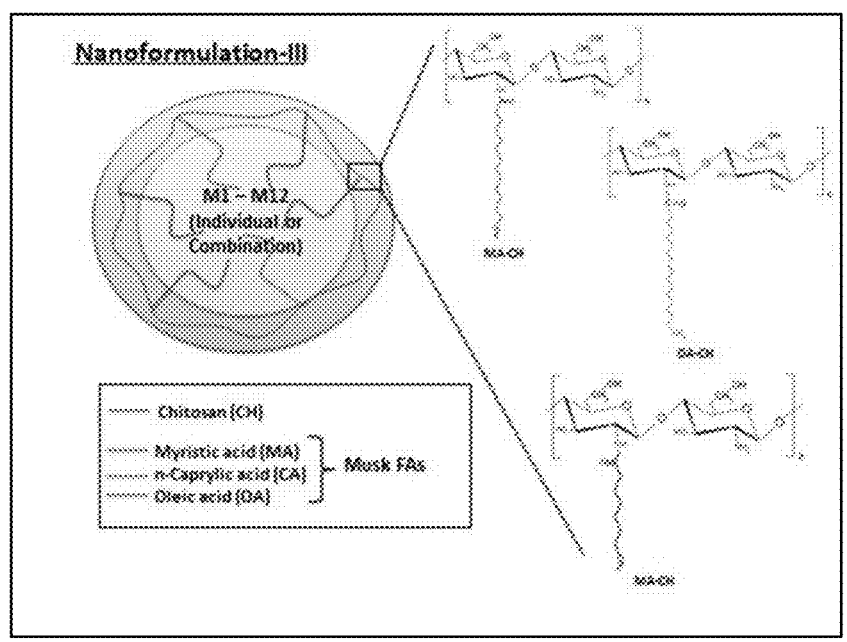
FIG. 3 depicts Nano-encapsulation of musk derived bioactive compounds (M1 and/or M2) with anti-microbial and fragrance characteristics using natural chitosan cross linked with Musk derived fatty acids, in accordance with embodiments of the present invention.

FIG. 3 depicts Nano-encapsulation of musk derived bioactive compounds (M1 and/or M2) with anti-microbial and fragrance characteristics using natural chitosan cross linked with Musk derived fatty acids, in accordance with embodiments of the present invention.

Figure 4:
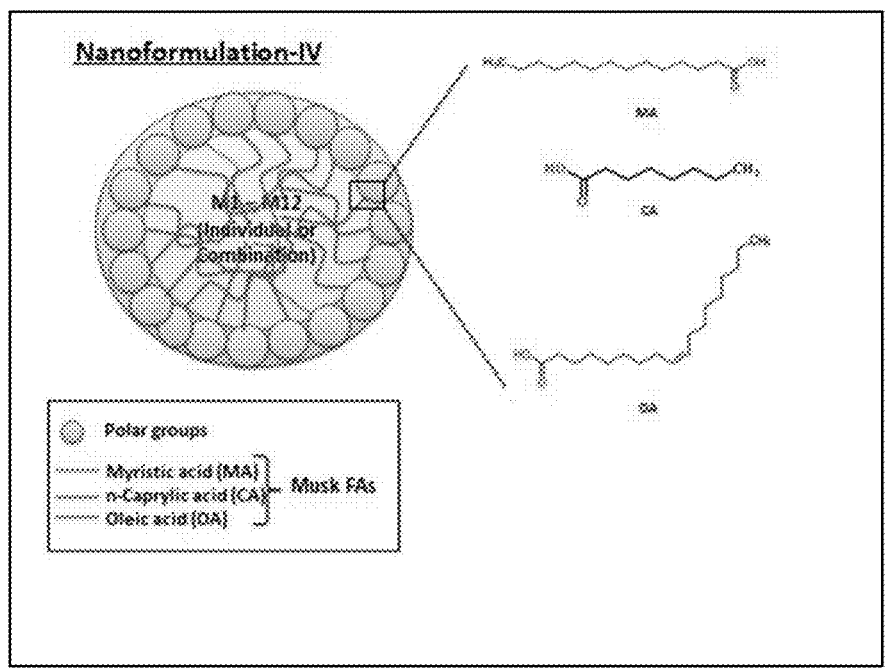
FIG. 4 depicts Nano-encapsulation of musk derived bioactive compounds (M1 and/or M2) with anti-microbial and fragrance characteristics using Musk derived fatty acids.

FIG. 4 depicts Nano-encapsulation of musk derived bioactive compounds (M1 and/or M2) with anti-microbial and fragrance characteristics using Musk derived fatty acids.

Figure 5:
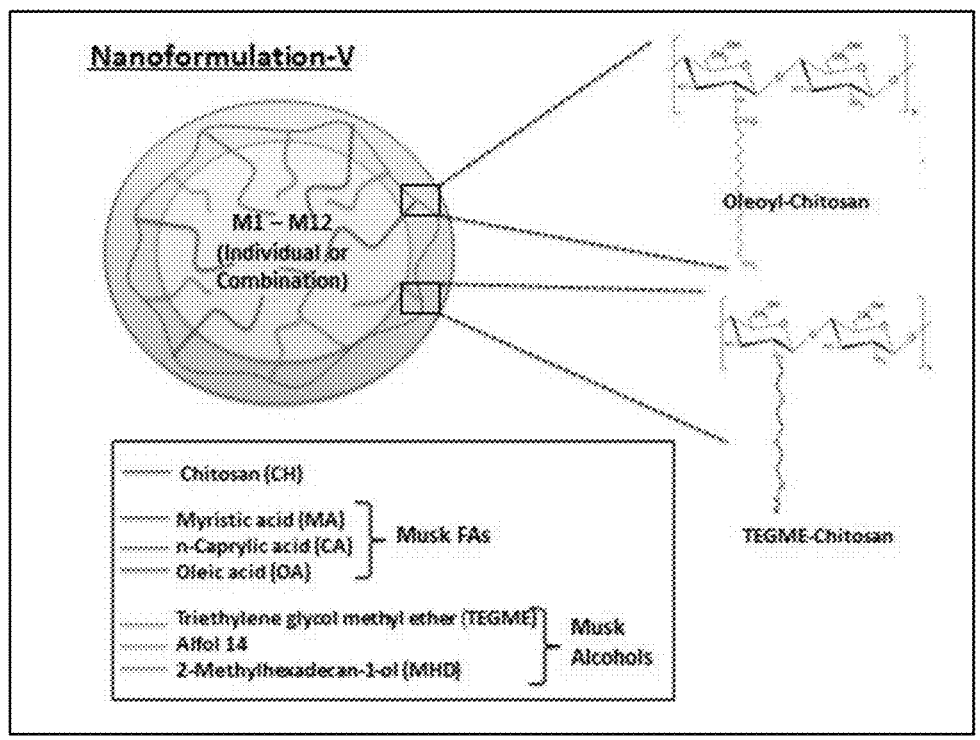
FIG. 5 depicts Nano-encapsulation of musk derived bioactive compounds (M1 and/or M2) with anti-microbial and fragrance characteristics using natural chitosan cross linked with Musk derived fatty acids and alcohol, in accordance with embodiments of the present invention.

FIG. 5 depicts Nano-encapsulation of musk derived bioactive compounds (M1 and/or M2) with anti-microbial and fragrance characteristics using natural chitosan cross linked with Musk derived fatty acids and alcohol, in accordance with embodiments of the present invention.

FIG. 1-5, Musk derived products such as M1 and/or M2 are chemically conjugated to HA polymer, FA polymer, CH polymer, HA-CH co-polymer, FA-CH co-polymer or HA-CH-FA co-polymer to be incorporated into the fabric of the textile products (carpet/rugs or clothes). Table 1: Diameter of inhibition zone of 3-hydroxyl p-Anisaldehyde ($C_8H_8O_3$) and p-Hydroxy-acetophenone (C8H8O2) compounds against *Aspergillus niger, Aspergillus fumigatus, Aspergillus flavus, Fusarium oxysporum, Candida albicans Staphylococcus aureus* and *Pseudomonas aeruginosa*

| Test Organisms | Diameter of inhibition Zone (mm) |
|---|---|
| Control | 00.00 |
| Aspergillus niger | 32.00 |
| Aspergillus fumigatus | 27.50 |
| Aspergillus flavus | 15.00 |
| Candida albicans | 23.00 |
| Staphylococcus aureus | 20.00 |
| Pseudomonas aeroginosa | 18.00 |

TABLE 2

Bioactive Compounds Isolated from Musk Extracts

| Musk Extracts | Structure | Symbol |
| --- | --- | --- |
| Vanillin | 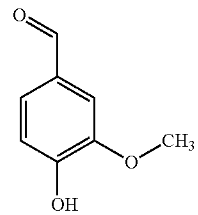 | M1 |
| O-Benzyl-L-serine | 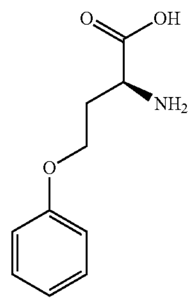 [SMILES: N[C@@H](CCOc1ccccc1)C(=O)O] | M2 |
| N-Cbz-L-tyrosine | 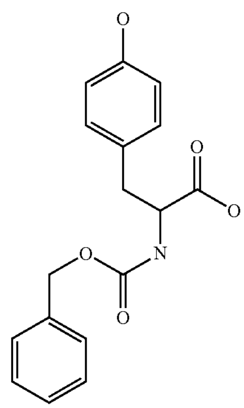 [SMILES: O=C(NC(Cc1ccc(O)cc1)C(=O)O)OCc1ccccc1] | M3 |
| Benzyloxycarbonyl-L-arginine | 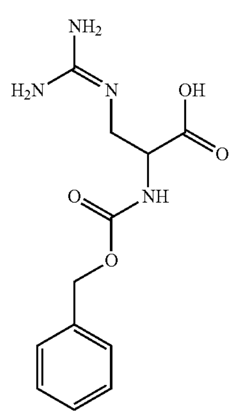 [SMILES: NC(N)=NCC(NC(=O)OCc1ccccc1)C(=O)O] | M4 |
| Benzoic acid, 4-hydroxyl-3-methoxy | 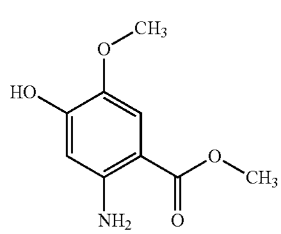 | M5 |

TABLE 2-continued

Bioactive Compounds Isolated from Musk Extracts

| Musk Extracts | Structure | Symbol |
|---|---|---|
| P-Anisaldehyde, 3-hydroxy | 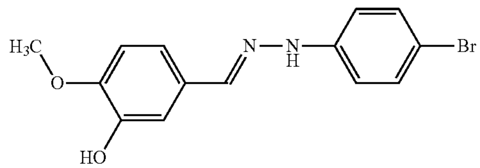 [SMILES: COc1ccc(/C=N/Nc2ccc(Br)cc2)cc1O] | *M6 |
| Acetophenone,4'-hydroxyl- 3', 5'-dimethoxy | 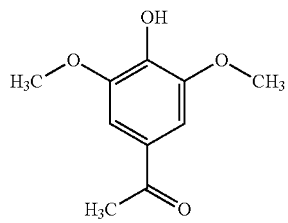 | *M7 |
| Diisooctyl phthalate | 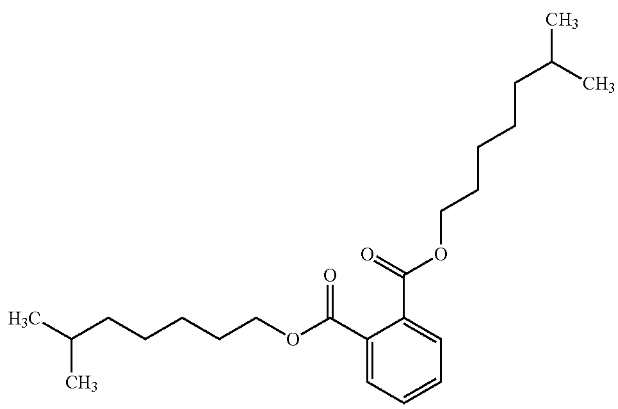 [SMILES: CC(C)CCCCCOC(=O)c1ccccc1C(=O)OCCCCCC(C)C] | M8 |
| Diethyl Phthalate | 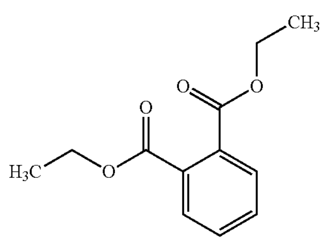 [SMILES: CCOC(=O)c1ccccc1C(=O)OCC] | M9 |
| Musk ambrette Benzene, 1-[1,1-dimethylethyl]2-methoxy-4-methyl-3,5-dinitro | 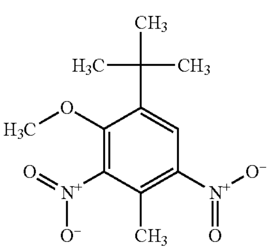 [SMILES: COc1c(C(C)(C)C)cc([N+](=O)[O-])c(C)c1[N+](=O)[O-]] | M10 |
| Isobutyl phthalate | 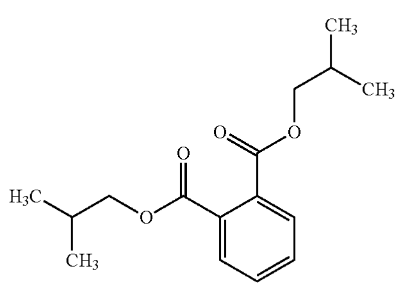 [SMILES: CC(C)COC(=O)c1ccccc1C(=O)OCC(C)C] | M11 |

TABLE 2-continued

Bioactive Compounds Isolated from Musk Extracts

| Musk Extracts | Structure | Symbol |
|---|---|---|
| Diisooctyl phthalate | 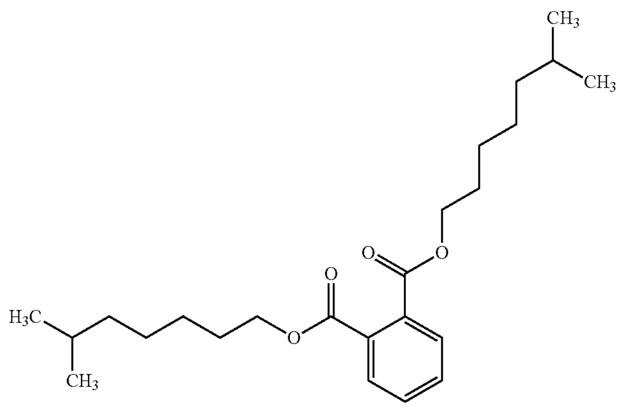 [SMILES: CC(C)CCCCCOC(=O)c1ccccc1C(=O)OCCCCCC(C)C] | M12 |
| Myristic acid | 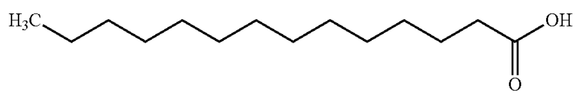 [SMILES: CCCCCCCCCCCCCC(=O)O] | MA |
| n-Caprylic acid | 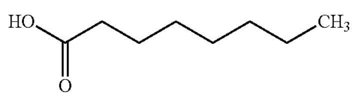 | CA |
| Oleic acid | 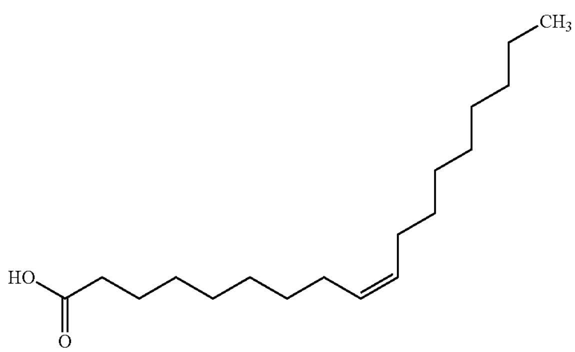 [SMILES: CCCCCCCC/C=C\CCCCCCCC(=O)O] | OA |
| Triethylene glycol methyl ether | 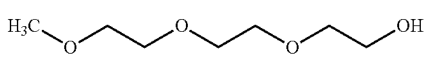 | TEGME |
| Alfol 14 | 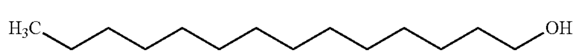 | Alfol 14 |
| 2-Methylhexadecan-1-ol | 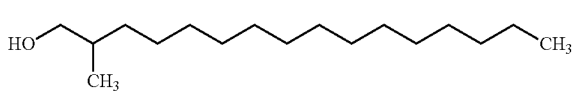 [SMILES: CCCCCCCCCCCCCCC(C)CO] | MHD |

*M6 and *M7 have synergistic antimicrobial activity (Against Aspergillus Niger, Aspergillus fumigetus, Aspergillus flavus, Fusarium oxysporium)

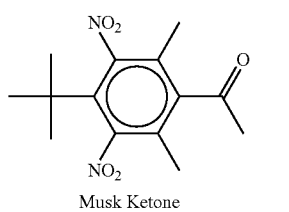

Musk Ketone

-continued

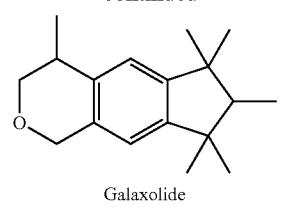

Galaxolide

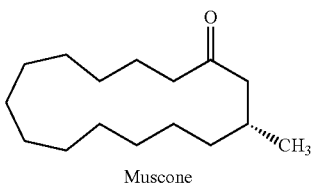

Muscone

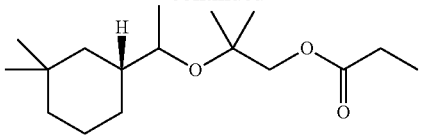

Alicyclic musks (cycloakyl ester)

Bioactive Compounds in Musk Extract

TABLE 3

| Musk Extracts (I, II, III, IV) | | | |
|---|---|---|---|
| Extract "I" | Extract "II" | Extracts "III" | Extract "IV" |
| Vanillin | Dihydroergotamine | [2S,3S]-[+]-2,3-Butanediol | Heptanol |
| O-Benzyl-L-serine | N-Methyl-2-pyrrolidone | 1-Methoxy-2-propyl acetate | n-Caprylaldehyde |
| N-Cbz-L-tyrosine | 2-Methyl-4,5-tetramethylene-5-ethyl-2-oxazoline | n-Nonanal | n-Nonanal |
| Benzyloxycarbonyl-L-arginine | Prolog [1,2-a]pyrazine-1,4-dione, hexahydro-3-[2-methylpropyl] | n-Doccosane | n-Hepatadecane |
| Myristic acid | Acetophenone, 4'-hydroxy-3',5'-dimethoxy | Hexadecanal cyclic ethylene acetal | Diethyl Phthalate |
| Benzoic acid, 4-hydroxyl -3-methoxy | Phenol, o-ter-butyl | 3-Pentanol, 2,4-dimethyl | Fornesan |
| Benzoic acid 3, hydroxy | Uracil, 1,3,5-trimethyl | Alfol 14 | n-Heptadecane |
| Benzoic acid 4, hydroxy | Phenol, 2,4- di-tert-butyl | n-Nonylphenol | Benzene, 1-[1,1-dimethylethyl]2-methoxy-4-methyl-3,5-dinitro |
| Ethanone, 1- [4-hydroxy-3-methoxyphenyl] | Acetophenone,4'-hydroxyl- 3',5'-dimethoxy | n-pentadecane | Isobutyl phthalate |
| Ethanone, 1- [4-hydroxyphenyl] | | Isobutyl phthalate | n-Nonadecane |
| P-Anisaldehyde, 3-hydroxy | | 1,2-Benzenedicarboxylic acid, dibutyl ester | Oleic acid |
| Isobutyric acid | | Eicosane | n-Heneicosane |
| n- Butyric acid | | Heneicosane | Diisooctyl phthalate |
| [s]-[+]-3-Methyl-2-butanol | | n-Hexatriacontane | |
| Butanoic acid, 3-methyl | | Hexanedioic acid, diisooctyl ester | |
| 2- Methyl butanoic acid | | 2-Methylhexadecan-1-ol | |
| Pentanoic acid | | Diisooctyl phthalate | |
| Acetoin | | | |
| n-Hexanoic acid | | | |
| Benzylaxycarbonyl-L-arginine | | | |
| N-Cbz-L-tyrosine | | | |
| Benzyl alcohol | | | |
| Heptoic acid | | | |
| Benzeneethanol | | | |
| 3-Methyl-3-heptanol | | | |
| n-Caprylic acid | | | |
| Retardex | | | |
| B-Hydroxyethyl phenyl ether | | | |
| Phenylacetic acid | | | |
| Phenol, o-tert-butyl | | | |
| O-benzyl-L-serine | | | |
| Phenylpropionic acid | | | |

Bioactive Compounds in Musk Extracts

TABLE 4

| Musk Extracts "I": | |
| --- | --- |
| Extract "I" | Structure |
| Vanillin | *4-hydroxy-3-methoxybenzaldehyde structure* |
| O-Benzyl-L-serine | *O-benzyl-L-serine structure* |
| N-Cbz-L-tyrosine | *N-Cbz-L-tyrosine structure* |
| Benzyloxycarbonyl-L-arginine | *Cbz-L-arginine structure* |
| Myristic acid | $H_3C-(CH_2)_{12}-COOH$ |

TABLE 4-continued

| Musk Extracts "I": | |
|---|---|
| Extract "I" | Structure |
| Benzoic acid, 4-hydroxyl-3-methoxy | [structure: methyl 2-amino-4-hydroxy-5-methoxybenzoate] |
| Benzoic acid 3, hydroxy | [structure: 3-hydroxybenzoic acid] |
| Benzoic acid 4, hydroxy | [structure: 4-hydroxybenzoic acid] |
| Ethanone, 1-[4-hydroxy-3-methoxyphenyl] | [structure: acetovanillone] |
| Ethanone, 1-[4-hydroxyphenyl] | [structure: 4'-hydroxyacetophenone] |
| P-Anisaldehyde, 3-hydroxy | [structure: (4-bromophenyl)hydrazone of 3-hydroxy-4-methoxybenzaldehyde] |
| Isobutyric acid | [structure: isobutyric acid] |
| n-Butyric acid | [structure: n-butyric acid] |
| [s]-[+]-3-Methyl-2-butanol | [structure: 3-methyl-2-butanol] |

TABLE 4-continued

| Musk Extracts "I": | |
|---|---|
| Extract "I" | Structure |
| Butanoic acid, 3-methyl | |
| 2-Methyl butanoic acid | |
| Pentanoic acid | |
| Acetoin | |
| n-Hexanoic acid | |
| Benzyl alcohol | |
| Heptoic acid | |
| Benzeneethanol | |
| 3-Methyl-3-heptanol | |
| n-Caprylic acid | |
| Benzoic acid | |
| 2-Phenoxy ethanol | |

TABLE 4-continued

Musk Extracts "I":

| Extract "I" | Structure |
| --- | --- |
| Phenylacetic acid | *(structure: phenyl-CH₂-COOH)* |
| Phenol, o-tert-butyl | *(structure: 2-tert-butylphenol)* |
| O-benzyl-L-serine | *(structure)* |
| Phenylpropionic acid | *(structure: 2-phenylpropionic acid)* |

TABLE 5

Musk Extracts "II":

| Extract "II" | Structure |
| --- | --- |
| Dihydroergotamine | *(structure)* |
| N-Methyl-2-pyrrolidone | *(structure)* |
| 2-Methyl-4,5-tetramethylene-5-ethyl-2-oxazoline | *(structure)* |
| Pyrrolo [1,2-a] pyrazine-1,4-dione, hexahydro-3-[2-methylpropyl] | *(structure)* |

TABLE 5-continued
Musk Extracts "II":
| Extract "II" | Structure |
|---|---|
| Phenol, 2[1,1-dimethylethyl] 2-tert-butylphenol | 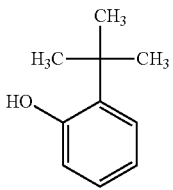 |
| Uracil, 1,3,5-trimethyl | 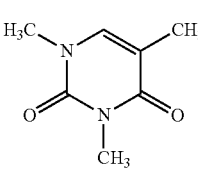 |
| Phenol, 2,4-di-tert-butyl | 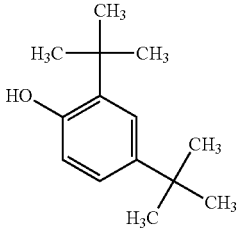 |
| Acetophenone, 4'-hydroxyl-3', 5'-dimethoxy | 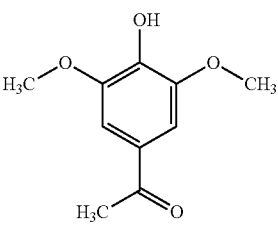 |
| 2-Piperidone | 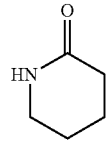 |
| Triethylene glycol methyl ether | 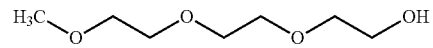 |
TABLE 6
Musk Extracts "III":
| Extracts "III" | Structure |
|---|---|
| [2S,3S]-[+]-2,3-Butanediol | 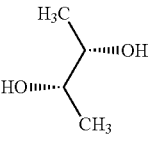 |
| 1-Methoxy-2-propyl acetate | 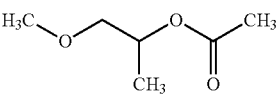 |
| n-Nonanal | 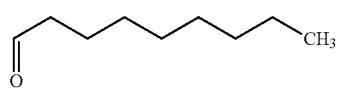 |
| n-Doccosane | 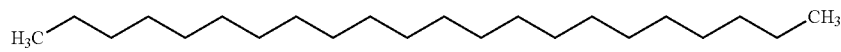 [SMILES: CCCCCCCCCCCCCCCCCCCCCC] |

TABLE 6-continued

Musk Extracts "III":

| Extracts "III" | Structure |
|---|---|
| Hexadecanal cyclic ethylene acetal | (structure) |
| 3-Pentanol, 2,4-dimethyl | (structure) |
| Alfol 14 | (structure) |
| n-Nonylphenol | (structure) |
| n-pentadecane | (structure) |
| Isobutyl phthalate | (structure) |

TABLE 6-continued

Musk Extracts "III":

| Extracts "III" | Structure |
|---|---|
| 1,2-Benzene-dicarboxylic acid, dibutyl ester | 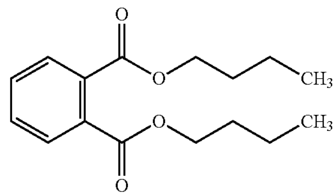 [SMILES: CCCCOC(=O)c1ccccc1C(=O)OCCCC] |
| Eicosane | 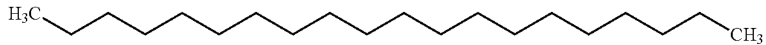 [SMILES: CCCCCCCCCCCCCCCCCCCC] |
| Heneicosane | 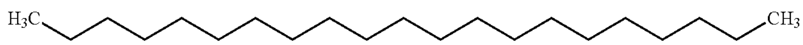 [SMILES: CCCCCCCCCCCCCCCCCCCCC] |
| n-Hexa-triacontane | 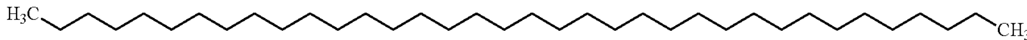 [SMILES: CCCCCCCCCCCCCCCCCCCCCCCCCCCCCCCCCCCC] |
| Hexanedioic acid, diisooctyl ester | 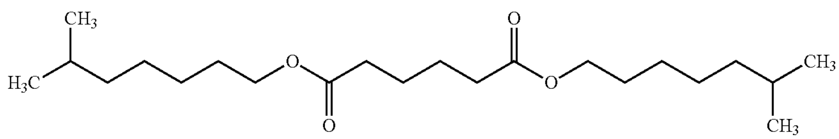 [SMILES: CC(C)CCCCCOC(=O)CCCCC(=O)OCCCCCC(C)C] |
| 2-Methylhexa-decan-1-ol | 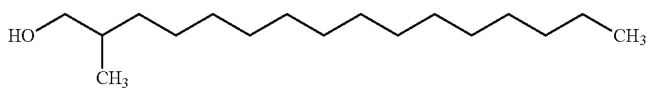 [SMILES: CCCCCCCCCCCCCCC(C)CO] |
| Diisooctyl phthalate | 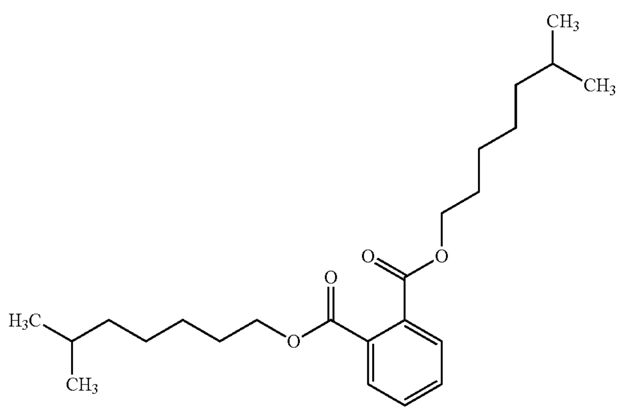 [SMILES: CC(C)CCCCCOC(=O)c1ccccc1C(=O)OCCCCCC(C)C] |

TABLE 7

Musk Extracts "IV":

| Extract "IV" | Structure |
|---|---|
| Heptanol | 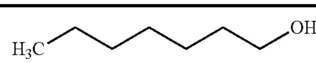 |
| n-Caprylaldehyde | 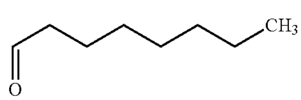 |
| n-Nonanal | 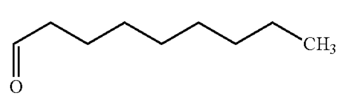 |
| n-Hepatadecane | 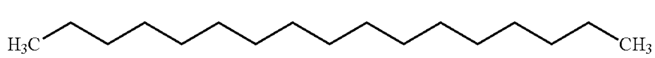 |

TABLE 7-continued
| Musk Extracts "IV": | |
|---|---|
| Extract "IV" | Structure |
| Diethyl Phthalate | 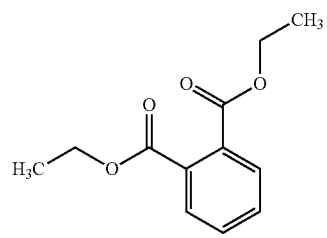 |
| Dodecane, 2,6,10-trimethyl | 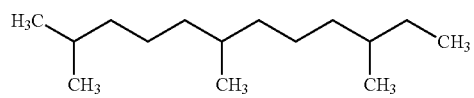 |
| n-Heptadecane | 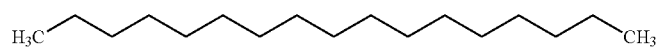 |
| Musk ambrette Benzene, 1-[1,1-dimethylethyl]2-methoxy-4-methyl-3,5-dinitro | 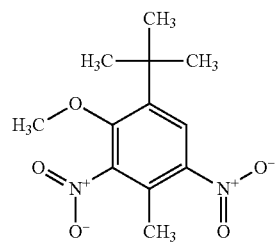 [SMILES: COc1c(C(C)(C)C)cc([N+](=O)[O-])c(C)c1[N+](=O)[O-]] |
| Isobutyl phthalate | 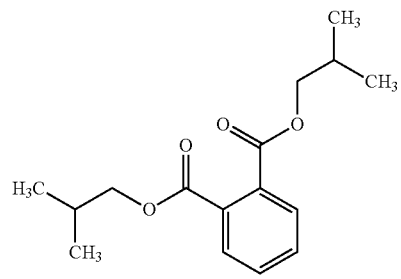 |
| n-Nonadecane | 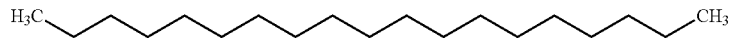 [SMILES: CCCCCCCCCCCCCCCCCCC] |
| Oleic acid | 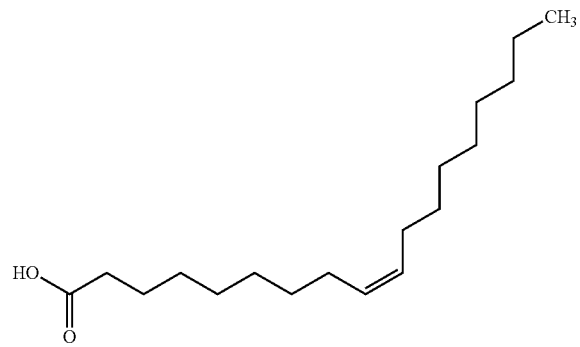 [SMILES: CCCCCCCC/C=C\CCCCCCCC(=O)O] |
| n-Heneicosane | 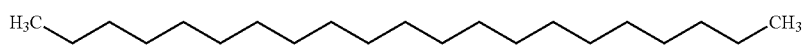 |

TABLE 7-continued

Musk Extracts "IV":

| Extract "IV" | Structure |
|---|---|
| Diisooctyl phthalate | 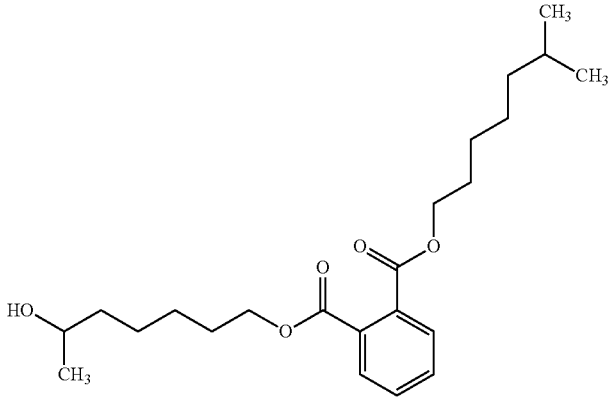 [SMILES: CC(C)CCCCCOC(=O)c1ccccc1C(=O)OCCCCCC(C)O] |

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A composition, comprising:
a nano-polymer comprising HA-CH co-polymer such that HA is cross-linked with CH, FA-CH co-polymer such that FA is cross-linked with CH, or HA-CH-FA co-polymer such that HA and FA are cross-linked with CH, wherein CH denotes chitosan, wherein HA denotes hyaluronic acid, and wherein FA denotes fatty acids; and
a compound encapsulated within the nano-polymer, said compound extracted from musk and chemically conjugated to the HA-CH co-polymer if the nano-polymer comprises the HA-CH co-polymer, the FA-CH co-polymer if the nano-polymer comprises the FA-CH co-polymer, or the HA-CH-FA co-polymer if the nano-polymer comprises the HA-CH-FA co-polymer, wherein the compound extracted from musk is selected from the group consisting of P-hydroxyacetophenone, hydroxyl P-Anisaldehyde, and O-Benzyl-L-serine.

2. The composition of claim 1, where the compound extracted from musk is P-hydroxyacetophenone.

3. The composition of claim 1, wherein the compound extracted from musk is hydroxyl P-Anisaldehyde.

4. The composition of claim 1, wherein the compound extracted from musk is O-Benzyl-L-serine.

5. The composition of claim 1, wherein nano-polymer comprises the HA-CH co-polymer.

6. The composition of claim 1, wherein nano-polymer comprises the FA-CH co-polymer.

7. The composition of claim 1, wherein nano-polymer comprises the HA-CH-FA co-polymer.

8. A textile product, comprising:
a carpet or clothes,
wherein the nano-polymer of claim 1 is incorporated into fabric of the carpet or clothes.

* * * * *